United States Patent [19]

Parekh

[11] Patent Number: 4,619,999
[45] Date of Patent: Oct. 28, 1986

[54] ALIPHATIC ISOCYANATE COMPOUNDS

[75] Inventor: Girish G. Parekh, Fairfield, Conn.

[73] Assignee: American Cyanamid Company, Stamford, Conn.

[21] Appl. No.: 466,755

[22] Filed: Feb. 15, 1983

[51] Int. Cl.$^4$ .................. C07D 251/00; C07C 118/00; C08G 12/30; C08G 12/12

[52] U.S. Cl. ........................................ 544/196; 560/29; 560/335; 560/337; 528/254; 528/259; 528/266

[58] Field of Search ...................... 260/453 AL, 453 P; 544/196; 560/29, 335, 337; 528/254, 259, 266

[56] References Cited

U.S. PATENT DOCUMENTS 3,144,468  8/1964  Hoover et al. ............... 260/453 AL

*Primary Examiner*—Alan Siegel
*Attorney, Agent, or Firm*—John W. Cornell; Henry C. Jeanette; Steven J. Hultquist

[57] ABSTRACT

An aliphatic isocyanate compound containing at least one N-methylene isocyanate group of the formula:

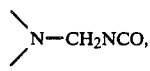

formed as a reaction product of isocyanic acid and a compound containing at least one N-alkoxymethyl group of the formula:

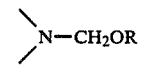

wherein R is $C_1$–$C_8$ alkyl.

5 Claims, No Drawings

ALIPHATIC ISOCYANATE COMPOUNDS

This invention relates to aliphatic isocyanate compounds which are particularly useful in coatings, foams, elastomers, and the like.

Polyfunctional isocyanates have been found useful in a number of applications, including for example their use as components in polyurethane coating formulations, in reaction injection molding (RIM) applications and as cross-linking agents. Aliphatic isocyanates are particularly desirable since products derived from them are light stable in character. Presently available polyfunctional isocyanates, aliphatic and aromatic, however, have low molecular weights and consequently high vapor pressures. Characteristically they are toxic and hazardous to handle.

Heretofore, isocyanic acid has been used to prepare aliphatic isocyanates by addition reaction with olefinic compounds, such as methyl styrene and alkylvinyl ethers. Although the resulting isocyanates are aliphatic and thus suitable for preparing light-stable products, such compounds in general have high vapor pressure.

It is therefore an object of this invention to provide aliphatic isocyanate compounds having light stability imparting properties, low vapor pressure and toxicity.

The aliphatic isocyanate compound of this invention contains at least one N-methylene isocyanate group of the formula:

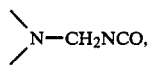

formed as a reaction product of isocyanic acid and a compound containing at least one N-alkoxymethyl group of the formula:

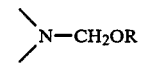

wherein R is $C_1$-$C_8$ alkyl.

Although the transetherification of free N-alkoxymethyl groups using carboxylic acids or alcohols has been reported in the literature, the present invention is believed the first instance of reacting isocyanic acid with an N-alkoxymethyl group to yield an isocyanate product.

The N-alkoxymethyl compound employed in the reaction with isocyanic acid to produce the aliphatic isocyanate compound of this invention includes the following:
Monomeric hexamethoxymethylmelamine;
Polymeric hexamethoxymethylmelamine;
Alkylated urea-formaldehyde resins;
Alkylated ethylene urea-formaldehyde resins;
Alkylated dihydroxyethylene urea;
Alkylated dihydroxyethylene urea-formaldehyde re resins;
Alkylated glycoluril-formaldehyde resins;
Alkylated N-methylolacrylamide;
Alkylated N-methylolamides;
Alkylated N-methylolcarbamates.

Preferred N-alkoxymethyl compounds include hexamethoxymethylmalamine and tetramethoxymethylglycoluril.

The reaction between isocyanic acid and the N-alkoxymethyl compound may suitably be carried out in a solvent medium, e.g., toluene, and in the presence of a strong acid catalyst such as n-dodecylbenzene sulfonic acid. Preferably, a stoichiometric excess of isocyanic acid is utilized in the reaction.

The aliphatic isocyanate compounds of the invention may be employed to form a cross-linkably curing composition comprising the aliphatic isocyanate compound and a polymer containing a functionality which may be —OH, —COOH, —CONH$_2$, —NH$_2$ and —SH. Such cross-linkably curing compositions are useful in adhesives, coatings, foams and elastomers. A particularly suitable end use application is a polyurethane composition containing the aliphatic isocyanate and a polymer containing a plurality of free hydroxyl groups. Such polyurethane composition may be used to form light-stable coatings on a substrate by curing same thereon.

EXAMPLE I

To a suitably equipped reaction vessel, 80 ml. of 20% solution of hexamethoxymethylmelamine—Cymel ® 300 in toluene was charged, followd by 100 g. of 20% solution of cyanic acid in toluene, and 1 ml of 35% solution of n-dodecylbenzene sulfonic acid. To this reaction mixture 160 ml of toluene were added. The reaction mixture was heated to 65°-70° C. for 2 hours. After this period the reaction mixture was cooled to room temperature and later purged with nitrogen to remove unreacted cyanic acid. The reaction mixture was filtered to remove the white solids formed during the reaction. Toluene was removed from the filtrate. 5 g. of a syrupy water white product was obtained. The IR analysis showed the presence of —NCO groups. The titration of the syrup showed that the product contained at least 2 NCO groups per melamine.

EXAMPLE II

To a suitably equipped reaction vessel, 12.8 g. tetramethoxymethylglycoluril dissolved in 75 ml toluene, were added. To this were added 260 g. of 10% cyanic acid solution in toluene, and 2 ml of 35% n-dodecylbenzene sulfonic acid solution in toluene. The reaction mixture was heated to 55° C. for 5 hours. After this period the reaction mixture was cooled to room temperature and later purged with nitrogen to remove unreacted cyanic acid. The reaction mixture was filtered to remove the white solid formed during the reaction. Toluene was removed from the filtrate. The IR analysis showed the presence of —CH$_2$NCO, and —CH$_2$NH-COOCH$_3$ groups in the resulting product. The product had an NCO content of 19% by titration. When a stoichiometric amount of this product was blended with diethylenetriamine, there was an exothermic reaction and the mixture gelled in a few seconds.

EXAMPLE III

To a suitably equipped reaction vessel, were charged 300 g of 12.7% solution of cyanic acid in toluene and 10 g. of hexamethoxymethylmelamine. This reaction was heated to reflux for 30 minutes. After this period the reaction mixture was cooled to room temperature and allowed to stand overnight. Later it was sparged with nitrogen to remove unreacted cyanic acid and filtered to remove the white solids. Toluene was removed from the filtrate by distillation. The resulting water white syrupy product showed the presence of —NCO groups by I.R. analysis.

What is claimed is:

1. A method of making an aliphatic isocyanate compound, comprising reacting isocyanic acid with a compound containing at least one N-alkoxymethyl group of the formula

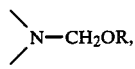

wherein R is $C_1$–$C_8$ alkyl, to form said aliphatic isocyanate containing at least one N-isocyanatomethyl group of the formula

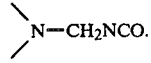

2. A method according to claim 1, wherein said N-alkoxymethyl compound is selected from the group consisting of monomeric or polymeric hexamethoxymethylmelamine; alkylated urea-formaldehyde resins; alkylated ethylene urea-formaldehyde resins; alkylated dihydroxyethyleneurea; alkylated dihydroxyethyleneurea-formaldehyde resins; alkylated glycoluril-formaldehyde resins; alkylated N-methylolacrylamide; alkylated N-methylolamides; and alkylated N-methylolcarbamates.

3. A method according to claim 1 wherein said reaction is carried out in the presence of a strong acid catalyst.

4. A method according to claim 1 wherein said N-alkoxymethyl compound is hexamethoxymethylmelamine.

5. A method according to claim 1 wherein said N-alkoxymethyl compound is tetramethoxymethylglycoluril.

* * * * *